United States Patent
Hall et al.

(10) Patent No.: US 9,957,705 B2
(45) Date of Patent: May 1, 2018

(54) HELICAL DRAIN FOR A TOILET

(71) Applicants: David R. Hall, Provo, UT (US); Dan Allen, Springville, UT (US); Jared Reynolds, Pleasant Grove, UT (US); Joshua Larsen, Spanish Fork, UT (US); Joe Fox, Spanish Fork, UT (US)

(72) Inventors: David R. Hall, Provo, UT (US); Dan Allen, Springville, UT (US); Jared Reynolds, Pleasant Grove, UT (US); Joshua Larsen, Spanish Fork, UT (US); Joe Fox, Spanish Fork, UT (US)

( * ) Notice: Subject to any disclaimer, the term of this patent is extended or adjusted under 35 U.S.C. 154(b) by 0 days. days.

(21) Appl. No.: 15/168,664

(22) Filed: May 31, 2016

(65) Prior Publication Data

US 2017/0198466 A1    Jul. 13, 2017

Related U.S. Application Data

(60) Provisional application No. 62/276,826, filed on Jan. 9, 2016.

(51) Int. Cl.
*E03D 11/02* (2006.01)
*E03D 11/06* (2006.01)

(52) U.S. Cl.
CPC .......... *E03D 11/06* (2013.01); *E03D 2201/30* (2013.01)

(58) Field of Classification Search
CPC ........................................................ A47K 1/02
USPC ...................................................... 4/300–442
See application file for complete search history.

(56) References Cited

U.S. PATENT DOCUMENTS

2017/0030063 A1*   2/2017   Godines .................... E03D 5/09
2017/0058500 A1*   3/2017   Garrels .................... E03D 9/038

\* cited by examiner

*Primary Examiner* — Lori Baker

(57) ABSTRACT

A helical drain for a toilet is disclosed. The present invention relates to a novel toilet drain configuration. Specifically, the novel toilet drain configuration comprises a helical loop trapway. The drain of the present invention exits the toilet bowl and forms a substantially vertical tubular loop running generally parallel to the width of the bowl or stool, or perpendicular to the longitudinal axis of the bowl or stool, before being connected to a sewer. The drain of the present invention functions like a P-trap syphon in removing the contents of the bowl. The diameter of the looped tubular portion of the drain may vary by approximately 20 percent or less in the direction of the sewer connection. Sensors may be placed on the drain to monitor drain contents, fluid levels, and drain performance. The drain may be fitted with valves to control the flow of fluids and gases through the drain.

16 Claims, 6 Drawing Sheets

HELICAL DRAIN FOR A TOILET

CROSS-REFERENCES

This patent application claims priority to U.S. Provisional Application No. 62/276,826, filed Jan. 9, 2016, entitled: A Looped Drain for a Toilet Bowl.

FIELD OF INVENTION

The present invention relates generally to the field of toilet drains, and more particularly to toilet drains that comprise a P-trap having a weir and spillway.

BACKGROUND

Traditional toilets have a plane of left-right symmetry, or an approximate plane of symmetry oriented vertically from the front of the toilet to the back. The P-trap style trapway or drain in a traditional toilet functions like a siphon in removing waste from a toilet bowl. The trapway remains substantially in the plane and therefore requires bends of differing curvatures to alternately form a trap and return water to the sewer. Due to the symmetry constraint, the flush jet typically enters the bowl from either the front or the back and vice-versa for the water exiting the bowl. Toilet drains utilizing a liquid P-trap style trapway typically comprise multiple bends, exiting the sump portion of the toilet bowl in a U-shape and following a course in a single vertical plane extending through the middle of the toilet from front to back. The bend in the drain creates a pipe section angled upwards to trap a column of water and isolate the sewer from the toilet bowl or sink. The pipe then bends over and back down again and empties into the sewer. From a side view, if the first bend has a positive curvature (bends up), the second bend has a negative curvature (bends down).

In a toilet, a water jet from a pressure source such as a tank or wall may enter the toilet bowl near the bottom. Water may also enter the bowl from the rim or another source of rinse water. One goal of low volume flush toilet design with a siphon flush is to fill the trapway completely with water as fast as possible, to "kick" or engage the siphon with minimal water. The higher the velocity of water, the lower volume flush is possible. In order to generate the kick, the siphon water enters the trapway faster than it is leaving. One possible way to implement such a strategy is to increase the resistance of the pipe section after the second bend, by corrugating the flow or reducing the pipe diameter. Both methods, however, limit the exit flow and increase the likelihood of a clog, in addition to making the toilet harder to plunge if a blockage does occur.

Accordingly, there is a need for improvements in the design of flush systems that rapidly inject water and reduce the incidence of drain clogging.

SUMMARY OF THE INVENTION

The present invention relates to a novel toilet drain configuration. Specifically, the novel toilet drain configuration comprises a helical loop trapway. In some configurations, the helical loop trapway may exit the toilet bowl from the side, which allows for a toilet having an out-of-plane flush jet opposite the entrance port for the helical loop trapway. The water from the flush jet enters the bowl substantially out-of-plane, for example from the right side, and exits the bowl via the modified helical loop trapway design that is substantially out-of-plane and opposite the jet.

This fundamental design change enables a host of beneficial design options. First, the water from the tank goes through a minimum of impeding bends, for instance bending only 90 degrees from the bottom of the tank to the side of the bowl. The quarter-bend turn may have a larger radius relative to the length of the pipe section compared to designs that have to bring the water from the tank in the back to the jet entrance at the front (a 180 degree bend). The shorter bend and distance allows the flush jet water to transit quickly from the tank (or other reservoir or pressure system) losing a minimum of momentum. Additionally, the diameter of the pipe may be large, as it is out-of-plane and does not need to be monolithic with the toilet bowl.

On the downstream side of the bowl, the flush system may form a trapway with a bend of substantially monotonic helicity. That means there is an axis for which the trapway looks like a corkscrew, the pipe forming a section of loop-de-loop, like an amusement park roller coaster ride turn that goes partially upside down. Downstream of the trap there may be deviations from the monotonic helicity, but in the vicinity of the trap the pipe bends does not change the sign of its curvature. Essentially the trapway may be formed from approximately a section of a torus (pipe bent into portion of a circle). This is radically different from traditions traps that bend alternately up and then down in different directions.

The high speed injection of flush jet water allows for a siphon flush with a larger trapway pipe, offering with less impedance. The looping trapway provides a minimum of resistance and allows objects transiting the trapway to continue in a quasi-laminar flow, reducing the likelihood of a clog. For example, compliant objects like feces may bend in the trapway to accommodate the pipe curvature. Because the pipe bend does not change many times, the feces may be more likely to transit without obstruction, relative to a design which forces the feces and other flush material to bend alternately one direction and then the other. The angular momentum of the flushing matter is significantly maintained through the trap.

A toilet with a skirted design can hide the out-of-plane flush jet pipe and trapway from the user, offering a smooth continuous outer surface for the toilet.

Accordingly, the present invention relates to a toilet drain comprising a helical loop trapway. In one embodiment, the helical loop trapway has substantially monotonic helicity. In another embodiment, the helical loop trapway has monotonic helicity from an entrance port of the helical loop trapway disposed at a toilet bowl exit upwardly to an apex of the helical loop trapway. In another particular embodiment, the helical trapway has monotonic helicity from the trapway entrance to the trapway exit.

In another aspect, the helical loop trapway of the present invention has a helical axis having a major directional component that is out of a vertical plane extending through a middle of the toilet from a toilet front to a toilet back.

In another aspect, the entrance port of the helical loop trapway is positioned on a side of a toilet bowl. In one embodiment, the toilet further comprises a flush water delivery port on a side of the toilet bowl opposing the entrance port of the helical loop trapway. Alternatively, in another embodiment, the flush water delivery port extends downwardly from a flush water reservoir through a right angle and to the flush water delivery port.

In another aspect, the helical loop trapway has at least a portion from an exit of the toilet bowl to a sewer line having a gradually narrowing internal diameter. In one embodiment, the helical loop trapway has an internal diameter that varies by 25 percent or less.

In another aspect, the helical loop trapway exits from a toilet bowl in a downward direction. In one embodiment, the toilet further comprises a flush water delivery port on a side of the toilet bowl opposing the trapway and oriented toward entrance in a downward direction.

In another aspect, the helical loop trapway has a center axis that extends out of a vertical front-to-back plane through the middle of the toilet.

In another aspect, the toilet comprises a toilet bowl for receiving waste, wherein the toilet bowl has an exit port for waste connected to an entrance port of the helical loop trapway for receiving flush water, and a standing water level, the exit port being below the standing water level and oriented substantially to one side, and the helical loop trapway has a portion elevated above the exit port and entrance port.

In another aspect, the entrance port is below the standing water level and opposes the exit port.

In another embodiment, the toilet of the present invention further comprises a water level sensor. In other embodiments, the toilet of the present invention may also comprise health sensors.

In another aspect, the toilet helical loop trapway comprising an entrance port configured to receive waste from a toilet bowl, a portion comprising a helical loop having monotonic helicity from the entrance port upwardly to at least an apex of the helical loop trapway, and an exit configured to exhaust waste into a sewer, wherein the helical loop portion comprises a portion that is elevated above the entrance and the exit.

In one embodiment, the portion comprising a helical loop having monotonic helicity extends from the entrance port upwardly through the apex of the helical loop trapway and to at least a portion that is oriented in a vertically downward direction.

BRIEF DESCRIPTION OF THE DRAWINGS

The present invention is illustrated and described in reference to the accompanying drawings in which.

Figure 1:
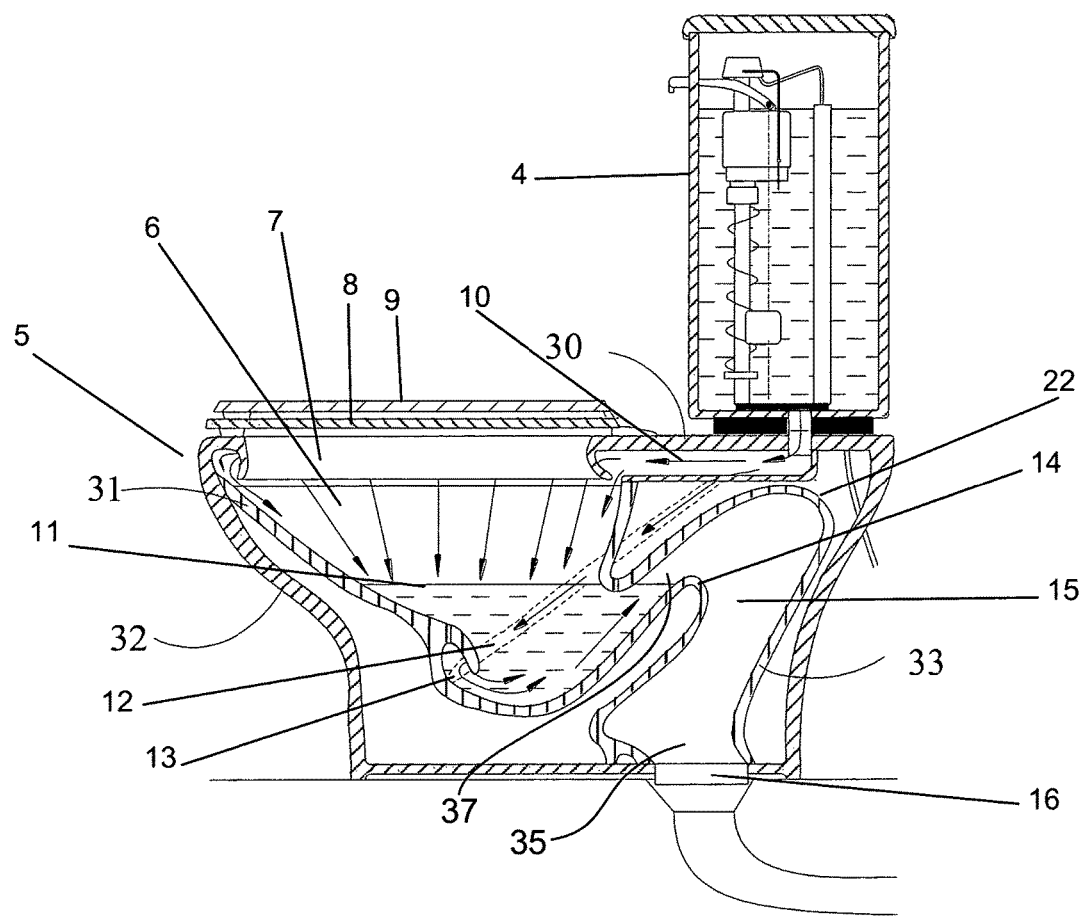
FIG. 1 is a side-view of a discrete modular hydraulic core comprising a toilet bowl and a tubular P-trap style drain having a weir and a spillway.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The skilled artisan will understand, however, that the apparatuses, systems and methods described below can be practiced without employing these specific details, or that they can be used for purposes other than those described herein. Indeed, they can be modified and can be used in conjunction with products and techniques known to those of skill in the art in light of the present disclosure. The drawings and descriptions are intended to be exemplary of various aspects of the invention and are not intended to narrow the scope of the appended claims. Furthermore, it will be appreciated that the drawings may show aspects of the invention in isolation and the elements in one figure may be used in conjunction with elements shown in other figures.

Reference in the specification to "one embodiment" or "an embodiment" means that a particular feature, structure, or characteristic described in connection with the embodiment is included in at least one embodiment, but is not a requirement that such feature, structure or characteristic be present in any particular embodiment unless expressly set forth in the claims as being present. The appearances of the phrase "in one embodiment" in various places may not necessarily limit the inclusion of a particular element of the invention to a single embodiment, rather the element may be included in other or all embodiments discussed herein.

Furthermore, the described features, structures, or characteristics of embodiments of the invention may be combined in any suitable manner in one or more embodiments. In the following description, numerous specific details are provided, such as examples of products or manufacturing techniques that may be used, to provide a thorough understanding of embodiments of the invention. One skilled in the relevant art will recognize, however, that embodiments of the invention may be practiced without one or more of the specific details, or with other methods, components, materials, and so forth. In other instances, well-known structures, materials, or operations are not shown or described in detail to avoid obscuring aspects of the invention.

Before the present invention is disclosed and described in detail, it should be understood that the present disclosure is not limited to any particular structures, process steps, or materials discussed or disclosed herein, but is extended to include equivalents thereof as would be recognized by those of ordinarily skill in the relevant art. More specifically, the invention is defined by the terms set forth in the claims. It should also be understood that terminology contained herein is used for the purpose of describing particular aspects of the invention only and is not intended to limit the invention to the aspects or embodiments shown unless expressly indicated as such. Likewise, the discussion of any particular aspect of the invention is not to be understood as a requirement that such aspect is required to be present apart from an express inclusion of the aspect in the claims.

It should also be noted that, as used in this specification and the appended claims, singular forms such as "a," "an," and "the" may include the plural unless the context clearly dictates otherwise. Thus, for example, it is understood that a reference to "an engagement element" may include one or more of such engagement elements. In particular, with respect to the construction of claims, it is further understood that a reference to "an engagement element" reads on an infringing device that has more than one engagement element, since such infringing device has "an engagement element", plus additional engagement elements. Accordingly, the use of the singular article "a," "an," and "the" is considered open-ended to include more than a single element, unless expressly limited to a single element by such language as "only," or "single."

As used herein, a plurality of items, structural elements, compositional elements, and/or materials may be presented in a common list for convenience. However, these lists should be construed as though each member of the list is individually identified as a separate and unique member.

The term "helical" means a loop having the general form of a helix or spiral. As used herein, the term "helical" does not require a constant angle of curvature or a uniform radius of curvature. Accordingly, the angle of curvature and radius of curvature may change within the helix. As used herein, the term "helical" may comprise a full revolution about an axis of the loop, or a partial revolution. The term "helical" further means that the pathway of curvature of the loop extends out of a single vertical plane.

The term "loop", as used in the context of a "trapway comprising a loop", means that a portion of the trapway is folded so as to include an upward rise and a downward fall of sufficient height to create a waterseal between the toilet bowl and the sewer line.

The term "monotonic," as used herein, means that the sign or direction of curvature does not change and is constant. As used in reference to the helical trapway of the present invention, "monotonic" specifically means that the trapway curves in the same direction, i.e., curving in either a right handed direction or curving in a left handed direction without changing the sign or direction of curvature The term "substantially", as used in the context of "substantially monotonic helicity" means that the helical trapway helix is monotonic from the toilet bowl exit through at least the upward flow of flush water within the helix to the apex of the trapway. A helical trapway having "substantially monotonic helicity" may have monotonic helicity from the toilet bowl exit through at least the upward flow of flush water within the helix, and subsequently change the sign of curvature at any position following the upward flow of flush water. In one particular embodiment, the helical trapway has a monotonic helicity from the exit of the toilet bowl exit through the upward flow of flush water continuing until the flush water flows vertically downward, after which point the helicity changes signs just prior to the helical trapway connecting to a sewer drain.

In one aspect, the present invention relates to a drain that exits the toilet bowl and forms a substantially vertical tubular loop running generally parallel to the width of the bowl or stool, or perpendicular to the length of the bowl or stool, before being connected to a sewer. The drain of the present invention functions like a P-trap siphon in removing the contents of the bowl. The diameter of the looped tubular portion of the drain may vary by approximately 20 percent or less in the direction of the sewer connection.

In another aspect, the toilet of the present invention may comprise a toilet bowl for receiving waste, wherein the toilet bowl has an exit port for waste connected to an entrance port of the helical loop trapway for receiving flush water, and a standing water level, the exit port being below the standing water level and oriented substantially to one side, and a helical loop trapway having a portion elevated above the exit port and entrance port. In one embodiment, the entrance port is below the standing water level and opposes the exit port.

In another aspect, the present invention relates to a helically looped tubular drain for a toilet bowl. The looped drain comprises a tube having an intermediate portion, a first end, and a second end. The first end portion exits a toilet bowl and the second end portion is adapted for connection to a sewer. The first end portion may comprise a hydraulic and or pneumatic jet. The intermediate portion is formed into a substantially vertical tubular loop generally parallel to the width of the stool or toilet bowl. A portion of the tubular vertical loop may comprise a spiral or a generally Archimedean spiral. The intermediate portion may comprise either a right-hand loop or a left-hand loop when viewed from the front of the bowl. The diameter of the tubular intermediate portion may vary from the first end portion to the second end portion. The tube's diameter at the first end may be greater than the tube's diameter at the second end. The intermediate portion may comprise a tubular P-trap siphon. The P-trap siphon may comprise a weir and a spillway. The weir may crest proximate a fill level, or static water level, in the bowl. The toilet bowl and drain may comprise one or more capacitive sensors. The intermediate portion may comprise one or more ports. At least one port may intersect the intermediate tubular portion at an angle of less than 90 degrees. At least one of the ports may be connected to a toilet ventilation system. At least one of the ports may be connected to a hydraulic and or pneumatic system. A deflector plate may be disposed within the intermediate portion proximate the ports. The toilet bowl and looped tubular drain of this invention may comprise a discrete modular hydraulic core or circuit. The diameter of the looped portion of the tubular drain may vary by approximately 20 percent or less in the direction of the sewer connection.

The present invention comprises a helical loop trapway for a toilet. In one embodiment, the helical loop trapway has substantially monotonic helicity. In another specific embodiment the helical loop trapway has monotonic helicity from an entrance port of the helical loop trapway disposed at a toilet bowl exit upwardly to an apex of the helical loop trapway.

In another embodiment, the helical loop trapway has a helical axis having a major directional component that is out of a vertical plane extending through a middle of the toilet from a toilet front to a toilet back. The helical axis of the trapway is the axis about which the helical trapway revolves or curves. An axis having a major directional component that is out of a vertical plane extending through a middle of the toilet from a toilet front to a toilet back means that the axis is out of the plane that extends vertically through the middle of the toilet from the from to the back of the toilet.

In another embodiment, the entrance port of the helical loop trapway is positioned on a side of a toilet bowl. By positioning the helical loop trapway entrance port to the side of the toilet bowl, the flush water delivery port that provides the hydraulic jet to can be positioned on the opposite side. The toilet further comprises a flush water delivery port on a side of the toilet bowl opposing the entrance port of the helical loop trapway. If the flush water delivery port is positioned on the opposite side of the helical loop trapway entrance port, water can be delivered from the water tank directly to the flush water delivery port with only a single 45° bend. The flush water delivery port extends downwardly from a flush water reservoir through a right angle and to the flush water delivery port. This avoids the necessity of a 180° bend in traditional toilets that have the flush water delivery port in the front of the toilet shooting a hydraulic jet to the rear of the toilet where the entrance port of the trapway is typically disposed, which slows the flow of the hydraulic jet and decreases its force.

In another aspect, the present invention further contemplates a helical loop trapway having at least a portion from an exit of the toilet bowl to a sewer line with a gradually narrowing internal diameter. In some specific embodiments, the helical loop trapway has an internal diameter that varies by 25 percent or less.

In some embodiments, the helical loop trapway exits from a toilet bowl in a downward direction. In embodiments in which the helical loop trapway exits from a toilet bowl in a downward direction, the toilet may further comprises a flush water delivery port on a side of the toilet bowl opposing the trapway and oriented toward the entrance in a downward direction so that a hydraulic jet is directed in the downward direction of the helical loop trapway exit.

In another aspect, the present invention provides a helical loop trapway having a center axis that extends out of a vertical front-to-back plane through the middle of the toilet. In this context, the "center axis" means the center of the hollow trapway tube or cylinder that defines the direction and course of the trapway. Thus, the center axis of the helical loop trapway is not in a single plane, but rather curves in a helical pattern outside of a single plane.

In another aspect, the helical loop trapway having substantially monotonic helicity may comprise an entrance port configured to receive waste from a toilet bowl, a portion comprising a helical loop having monotonic helicity from the entrance port upwardly to at least an apex of the helical loop trapway, and an exit configured to exhaust waste into a sewer, wherein the helical loop portion comprises a portion that is elevated above the entrance and the exit. In another embodiment, the portion comprising a helical loop having monotonic helicity extends from the entrance port upwardly through the apex of the helical loop trapway and to at least a portion that is oriented in a vertically downward direction. In another embodiment, the helical loop trapway has a substantially monotonic helicity from the trapway entrance to the trapway exit.

The toilet of the present invention, comprising a helical loop trapway, may further include diagnostic sensors configured to analyze the waste of a user. For example, the toilet may include a water level sensor configured to analyze the volume of waste. Other suitable health status sensors may include, for example, a spectrometer for detecting and analyzing particular chemical analytes in waste, such as blood urea nitrogen (BUN), glucose, creatinine, protein, urea, ketones, oxalate, and albumin. Particular analytes of interest may include metabolites, such as estrone-3-glucuronide ($E_1G$) a major estrogen metabolite, and the like.

The various aspects of the present invention are illustrated in the drawings, which show a particular embodiment of the invention. It is understood that other embodiments not illustrated in the figures are also contemplated as falling within the scope of the subject matter recited in the claims of the invention, set forth below.

FIG. 1 shows a toilet generally related to the field of the present invention. The toilet comprises a water tank 4 mounted on a toilet stool 5. The toilet stool 5 comprises a toilet bowl 6, a toilet bowl rim 7, a toilet seat 8, and a toilet seat lid 9. The toilet further comprises a flush water channel 10 running through the rim 7 and a jet water channel 12 for delivering water to the bowl jet 13. The toilet bowl further comprises a P-trap style tubular drain generally at 14, 15 comprising a weir 14 and a spillway 15. The drain is connected to a sewer 16. An entrance port 37 leads from toilet bowl 6 into the P-trap style tubular drain and an exit port 35 leads from the P-trap style tubular drain into the sewer. The static water level 11 in the bowl is proximate the crest of the weir 14. The hydraulic jet 13 is proximate and directed into the mouth of the drain.

FIG. 1 also shows a discrete modular hydraulic core or circuit 31 comprising a toilet bowl 6 and a tubular P-trap style drain 22, comprising a weir 14 and a spillway 15 adapted for connection to a sewer 16. The hydraulic circuit 31 further comprises a bowl jet 13 for delivering a high pressure stream of water into the P-trap. The bowl jet 13 may be adjacent an opening of the P-trap or within the opening of the P-trap. It may be desirable to place the jet further inside the tubular portion of the P-trap. The discrete hydraulic circuit 31 may be inserted into a toilet stool shell as depicted in FIG. 1. The circuit 31 is replaceable apart from the stool shell and may accommodate a variety of stool shell configurations. The circuit 31 may comprise a ceramic or porcelain material or a non-ceramic or porcelain material, such as glass, a natural or synthetic rubber, silicone, plastic, carbon fibers, iron, steel, stainless steel, titanium, brass, copper, wood, fiberglass, or a composite of such materials. The circuit 31 may be formed by a variety of manufacturing process, such as blowing, molding, casting, or machining appropriate to the nature of the material being used. The interior surfaces of the circuit 31 may be highly polished. The interior surfaces of the P-trap 22 may comprise shapes that promote the flow toward the sewer 16.

FIG. 1 further shows the discrete modular hydraulic circuit 31 inserted into a toilet stool shell 30, 32. The hydraulic circuit 31 comprises a P-trap style drain 33 extending from the toilet stool 30 or toilet bowl 6.

Figure 2:
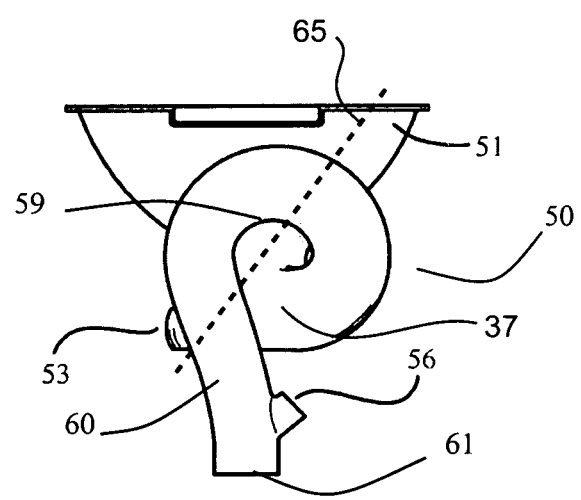
FIG. 2 is a rear-view of a discrete modular hydraulic core comprising a substantially vertical looped tubular drain in accordance with the present invention.

FIG. 2 shows a discrete modular hydraulic core or circuit as shown at 31, FIG. 1, showing more particularly the configuration of the looped drain. As shown, the discrete modular hydraulic circuit comprises a bowl 51 and a substantially vertical looped tubular drain 50. The entrance port 37 of the tubular drain 50 exits the bowl 51 and forms a loop comprising a crest 59. The center axis 65 of the substantially vertical loop runs generally parallel to the front-to-back length of bowl 51, or generally perpendicular to the side-to-side width of the bowl 51. As depicted the vertical loop of tubular drain 50 is a left-hand or counter-clockwise loop; alternatively, the vertical loop of tubular drain 50 may be a right-hand or clock-wise loop. A portion of the loop of tubular drain 50 may comprise a spiral, such as an Archimedean spiral. The drain may comprise a high-pressure jet 53 to assist in moving the contents of the bowl 51 over the crest 59 of vertical loop of tubular drain 50 to the second end of the drain 61. The vertical loop of tubular drain 50 may act as a siphon comprising a spillway 60 in removing the contents of the bowl 51 to the second end 61 adapted for connection to a sewer. The drain may comprise one or more ports 56. One of the ports 56 may intersect the drain at an angle of less than 90 degrees. The ports 56 may be connected to a hydraulic or pneumatic system. The tubular diameter of the vertical loop 50 may vary by approximately 20 percent or less in the direction of the sewer connection.

Figure 3:
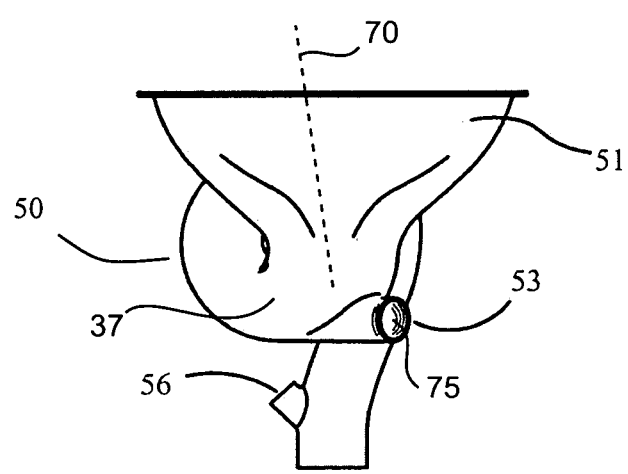
FIG. 3 is a front-view of a discrete modular hydraulic core comprising a substantially vertical looped tubular drain in accordance with the present invention.

FIG. 3 shows front view of the discrete modular hydraulic circuit of the present invention as shown in FIG. 2. The discrete modular hydraulic circuit comprises a toilet bowl 51, a looped tubular drain 50 exiting the bowl 51, an entrance port 37 connecting the bowl 51 with the looped tubular drain 50, a hydraulic jet 53 directed toward the mouth of the drain, and a port 56. The center axis of the tubular looped drain 50 runs generally parallel to the bowl 51, or generally perpendicular to the width of the bowl 51.

As viewed from the front, the drain forms a right-hand loop 50. Delivery port 75 provides the hydraulic jet into the tubular looped drain 50. The dashed arrow indicates the major directional component 70 of the tubular looped drain 50 which is nearly vertical.

Figure 4:
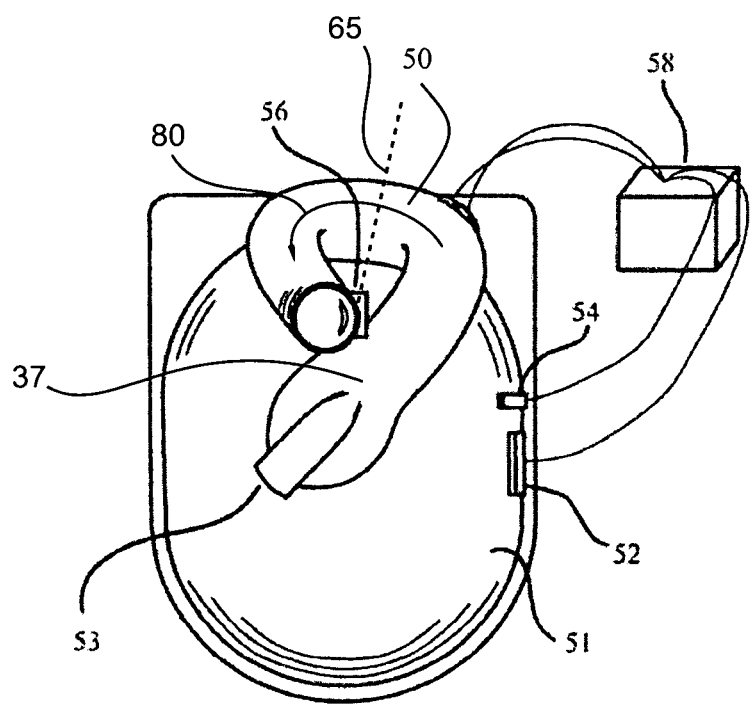
FIG. 4 is a bottom-view of a discrete modular hydraulic core comprising a substantially vertical looped tubular drain in accordance with the present invention.

FIG. 4 shows a bottom view of the discrete modular hydraulic circuit of the present invention. The discrete modular hydraulic circuit comprises a bowl 51, a generally looped tubular drain 50 exiting the bowl 51 at entrance port 37, and a port 56. The drain 50 comprises a high-pressure jet 53 disposed within the mouth of the drain. The bowl further comprises capacitive sensors 52 and 54 that are connected to a processor 58 comprising a power source, a capacitance analyzer and a central processing unit (CPU) for analyzing and comparing information from the capacitive sensors and correlating the information to the health of the user of the toilet bowl 51. The looped substantially vertical drain 50 runs generally parallel to the width of the bowl 51. Center axis 65 is shown by the dashed line which extends at an angle out of the page, nearly directly toward the viewer. Helical axis 80 is indicated by a solid arrow which follows the curvature of looped tubular drain 50.

Figure 5:
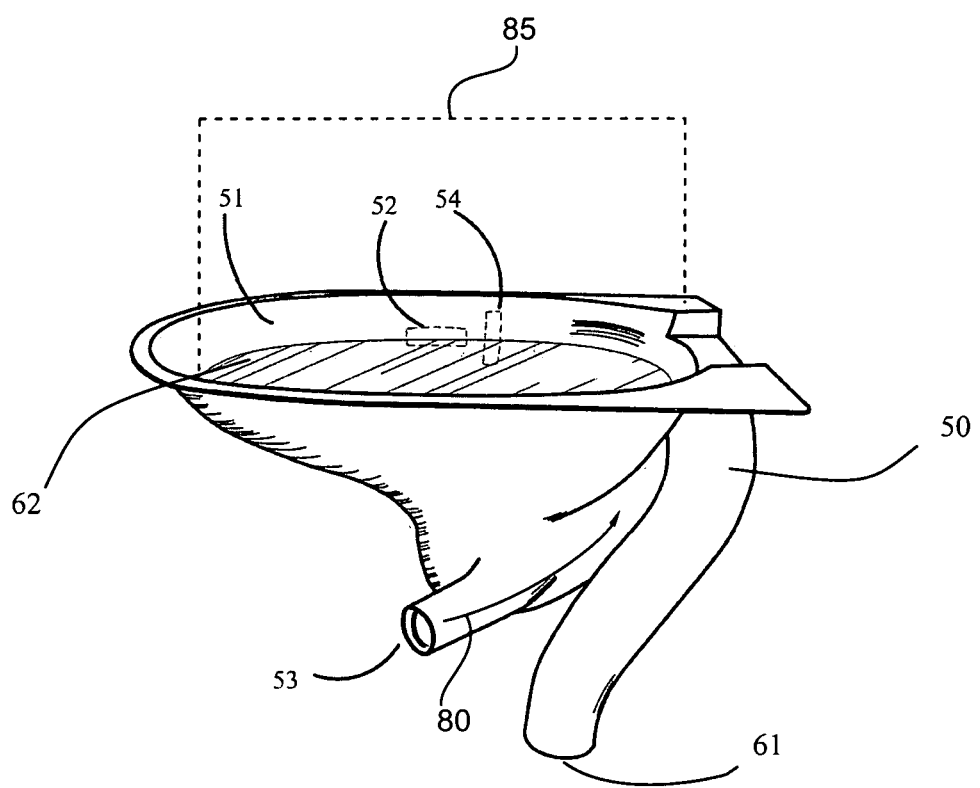
FIG. 5 is an elevated isometric-view of a discrete modular hydraulic core comprising a substantially vertical looped tubular drain in accordance with the present invention.

FIG. 5 is an elevated side view diagram of a discrete modular hydraulic core or circuit of the present invention. As shown the core comprises a toilet bowl 51 and a tubular P-trap style drain 50, comprising a weir and a spillway, not shown, adapted for connection to a sewer 61. The P-trap style drain 50 has a helical axis 80. Helical axis 80 is indicated by a solid arrow which follows the curvature of P-trap style drain 50. Center axis 65 extends out of the page and away from vertical front to back plane 85. The hydraulic core further comprises a jet 53 for delivering a high pressure stream of water into the P-trap 50. The jet 53 may be adjacent an opening of the P-trap or within the opening of the P-trap. It may be desirable to place the jet further inside the tubular portion of the P-trap. The discrete hydraulic core may be inserted into a toilet stool shell as depicted in FIG. 1. The circuit is replaceable apart from the stool shell and may accommodate a variety of stool shell configurations. The hydraulic core may comprise a ceramic or porcelain material or a nonceramic or porcelain material, such as glass, a natural or synthetic rubber, silicone, plastic, carbon fibers, iron, steel, stainless steel, titanium, brass, copper, wood, paper, vinyl, fiberglass, or a combination or composite of such materials. The hydraulic core may be formed by a variety of manufacturing processes, such as 3-D printing, additive layering, blowing, molding, blow molding, casting, or machining appropriate to the nature of the material being used. The surfaces of the core may be coated with water proof, wear resistant, and chemical resistant materials. The interior surfaces of the core may be polished. The interior surfaces of the P-trap 50 may comprise shapes that promote the flow toward the sewer connection 61 and discourage reverse flow. The hydraulic core may comprise capacitive sensors 52, 54 that may be conductive strips to detect the fill level, or static water level, 62 in the bowl 51. The capacitive sensors may be connected to a processor (as shown in FIG. 4 at 58) comprising a power source and an analyzer to correlate the water level in the bowl to a user's health and to control the functioning of the core.

Figure 6:
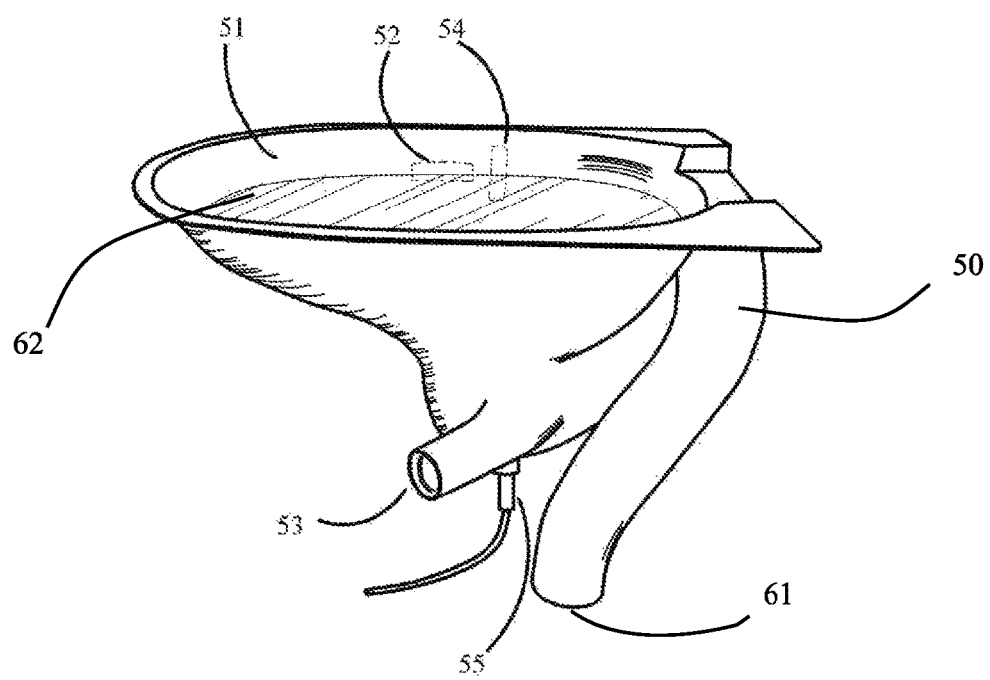
FIG. 6 is an elevated isometric-view of a discrete modular hydraulic core comprising a substantially vertical looped tubular drain in accordance with the present invention.

FIG. 6 is an elevated side view diagram of the discrete modular hydraulic core or circuit of the present invention. It is similar to the view shown in FIG. 5 with the addition of a pressure transducer 55 inserted into the core to aid in detecting changes in the contents of the bowl 51, and a side entry jet 53 that is disposed along the side of the P-trap 50 in order to provide a more dynamic flow though the P-trap 50. FIG. 6 also shows a processor 58 comprising a power source, a capacitance analyzer, and means for correlating the volume and rate of changes in the contents within the bowl 51 and P-trap 50 to a user's health, as well as to control the operation of the core. Also depicted is port 56 which intersects the P-trap at an angle of less than 90 degrees. The port 56 may be connected to a ventilation system, or to other hydraulic or pneumatic systems related to the operation of the core. The tubular diameter of the substantially vertical looped portion for the drain 50 may vary in the direction of the sewer connection by approximately 20 percent or less.

There is thus disclosed an improved toilet drain system. It will be appreciated that numerous changes may be made to the present invention without departing from the scope of the claims.

The invention claimed is:

1. A toilet comprising:
    a helical loop trapway;
    an entrance port, wherein the entrance port is disposed at a toilet bowl exit upwardly to an apex of the helical loop trapway, wherein the helical loop trapway has substantially monotonic helicity from the entrance port of the helical loop trapway; and
    a flush water delivery port on a side of the toilet bowl opposing the entrance port of the helical loop trapway.

2. The toilet according to claim 1, wherein the helical loop trapway has a helical axis having a major directional component that is out of a vertical plane extending through a middle of the toilet front to a toilet back.

3. The toilet according to claim 1, wherein the entrance port of the helical loop trapway is positioned on a side of a toilet bowl.

4. The toilet according to claim 3, wherein the flush water delivery port extends downwardly from a flush water reservoir through a right angle and to the flush water delivery port.

5. The toilet according to claim 1, wherein the helical loop trapway has at least a portion from an exit of the toilet bowl to a sewer line having a gradually narrowing internal diameter.

6. The toilet according to claim 1, wherein the helical loop trapway has an internal diameter that varies by 25 percent or less.

7. The toilet according to claim 1, wherein the helical loop trapway exits from a toilet bowl in a downward direction.

8. The toilet according to claim 7, wherein the toilet further comprises a flush water delivery port on a side of the toilet bowl opposing the trapway and oriented toward entrance in a downward direction.

9. The toilet according to claim 1, wherein the helical loop trapway has a center axis that extends out of a vertical front-to-back plane through the middle of the toilet.

10. The toilet according to claim 1, wherein the toilet comprises:
    a toilet bowl for receiving waste, wherein the toilet bowl comprises an exit port for waste connected to an entrance port of the helical loop trapway, and
    a standing water level,
    wherein the exit port is below the standing water level and oriented substantially to one side, and wherein the helical loop trapway has a portion elevated above the exit port and entrance port.

11. The toilet according to claim 10, wherein the entrance port is below the standing water level and opposes the exit port.

12. The toilet according to claim 10, wherein the helical trapway has a substantially monotonic helicity from the trapway entrance to the trapway exit.

13. The toilet according to claim 10, further comprising at least one capacitive sensor, wherein the at least one capacitive sensor detects the fill level or static water level of the toilet bowl.

14. The toilet according to claim 10, further comprising health sensors.

15. A toilet helical loop trapway comprising an entrance port configured to receive waste from a toilet bowl, a portion comprising:
- a helical loop having monotonic helicity from the entrance port upwardly to at least an apex of the helical loop trapway, and
- an exit configured to exhaust waste into a sewer, wherein the helical loop portion comprises a portion that is elevated above the entrance and the exit.

16. The toilet helical loop trapway according to claim 15, wherein the portion comprising a helical loop having monotonic helicity extends from the entrance port upwardly through the apex of the helical loop trapway and to at least a portion that is oriented in a vertically downward direction.

\* \* \* \* \*